United States Patent [19]

Pasqualini et al.

[11] Patent Number: 5,993,776
[45] Date of Patent: Nov. 30, 1999

[54] RADIOPHARMACEUTICAL COMPOSITIONS THAT INCLUDE AN INCLUSION COMPLEX OF A CYCLODEXTRIN AND A RADIO-HALOGENATED FATTY ACID

[75] Inventors: Roberto Pasqualini, Clamart; Bruno Perly, La Verriere; Laurent Mauclaire, Paris; Florence Djedaini-Pilard, Etampes; Yves Michel, Orsay, all of France

[73] Assignee: CIS bio International, Saclay, France

[21] Appl. No.: 08/836,196

[22] PCT Filed: Nov. 13, 1995

[86] PCT No.: PCT/FR95/01489

§ 371 Date: May 14, 1997

§ 102(e) Date: May 14, 1997

[87] PCT Pub. No.: WO96/14881

PCT Pub. Date: May 23, 1996

[30] Foreign Application Priority Data

Nov. 14, 1994 [FR] France .................................. 94 13609

[51] Int. Cl.$^6$ ............................ A61K 51/00; A61M 36/14
[52] U.S. Cl. ...................... 424/1.73; 424/1.11; 424/1.81; 424/1.85; 206/569; 206/223
[58] Field of Search .................................. 424/1.11, 1.37, 424/1.65, 1.73, 1.81, 1.85; 206/223, 569; 570; 536/103; 514/58; 106/269; 564/215; 554/124, 171; 525/50, 54.1

[56] References Cited

U.S. PATENT DOCUMENTS

| | | | |
|---|---|---|---|
| 5,024,998 | 6/1991 | Bodor ........................................ | 514/58 |
| 5,068,226 | 11/1991 | Weinshenker et al. .................... | 514/58 |
| 5,068,227 | 11/1991 | Weinshenker ............................. | 514/58 |
| 5,300,280 | 4/1994 | DeRosch et al. ........................ | 424/1.53 |
| 5,321,014 | 6/1994 | Janz et al. ................................ | 514/58 |
| 5,324,750 | 6/1994 | Lincoln et al. .......................... | 514/570 |
| 5,739,121 | 4/1998 | Wiebe et al. ............................. | 514/58 |

FOREIGN PATENT DOCUMENTS

| | | |
|---|---|---|
| 0 069 648 | 1/1983 | European Pat. Off. . |
| 0 149 197 | 7/1985 | European Pat. Off. . |

OTHER PUBLICATIONS

Dominique Duchene, Publ. de Sant, pp. 269–278 and 315–319, 1991, "New Trends in Cyclodextrins and Derivatives".

Daniel Fagret, et al., Eur. J. Nucl. Med., vol. 14, pp. 624–627, 1988, "Iodomethylated Fatty Acid Metabolism in Mice and Dogs".

Thierry Humbert, et al., Nucl. Med. Biol., vol. 17, No. 8, pp. 745–749, 1990, Influence of the Presence of a Methyl Group on the Myocardial Metabolism of 15–(Paraiodophenyl)–3 Methyl Pentadecanoic Acid (IMPPA).

J. Taki, et al., Nucl. Med. Communications, vol. 14, pp. 181–188, 1993, "$^{123}$I–Labelled BMIPP Fatty Acid Myocardial Scintigraphy in Patients with Hypertropic Cardiomyopathy: Spect Comparison with Stress $^{201}$T1".

P.R. Franken, et al., Nucl. Med. Comm., vol. 14, pp. 310–317, 1993, "Regional Distribution of $^{123}$I–(OrthoIodophenyl)–Pentadecanoic acid and $^{99}$Tc$^m$–MIBI in Relation to Wall Motion after Thrombolysis for Acute Myocardial Infarction".

Michael Eisenhut, et al., Nucl. Med. Biol., vol. 20, No. 6, pp. 747–754, 1993, "Metabolism of 15–(4'–[$^{123}$I] Iodophenyl–)Pentadecanoic Acid ([$^{123}$I]IPPA) In the Rat Heart; Identification of New Metabolites by High Pressure Liquid Chromatography and Fast Atom Bombardment–Mass Spectrometry".

*Primary Examiner*—José G. Dees
*Assistant Examiner*—Dameron Jones
*Attorney, Agent, or Firm*—Oblon, Spivak, McClelland, Maier & Neustadt, P.C.

[57] ABSTRACT

The invention relates to radio-pharmaceutical compositions that include an inclusion complex of a cyclodextrin and a radio-halogenated fatty acid.

These complexes include a cyclodextrin such as β-cyclodextrin, γ-cyclodextrin and their derivatives, and a radio-halogenated fatty acid, in particular a fatty acid labelled with radioactive iodine such as 16-iodo 3-methyl hexadecanoic acid suitable for the examination of the myocardium by scintigraphy.

The cyclodextrin allows the fatty acid to dissolve in aqueous solution without any addition of human blood albumin, while further improving the biodistribution of the fatty acid and its stability to heat.

20 Claims, 1 Drawing Sheet

RADIOPHARMACEUTICAL COMPOSITIONS THAT INCLUDE AN INCLUSION COMPLEX OF A CYCLODEXTRIN AND A RADIO-HALOGENATED FATTY ACID

This application is a 371 of PCT/FR95/01489 filed Nov. 13, 1995.

This invention has the objective of producing injectable radio-pharmaceutical compositions containing radio-halogenated fatty acids intended for the study of cardiac metabolism problems by scintigraphy.

The functional study of the heart by an external route allows to appraise possible pathological modifications. Hence, the image obtained by the injection of thallium-201 allows the display of the distribution of the blood flow in the myocardium, but it does not give any access to the metabolic condition of the myocardial cell.

The long chain fatty acids constitute one of the principal sources of energy of the cardiac muscle, since they supply 65% of the energy necessary for the functioning of the myocardial cells. As the presence of a halogen in these fatty acids does not modify in any way their metabolic properties, the radio-labelling of the fatty acids by a radioactive halogen therefore leads to an excellent method for exploring metabolic problems of the myocardial cells in man.

At the present time, in order to carry out these examinations, fatty acids labelled with radioactive iodine are used, such as 16-iodo($^{123}$I) 3-methyl hexadecanoic acid ($^{123}$IAGM). Within the nuclear medical departments, this product is prepared just before injection by labelling the IAGM with the iodine-123. This radio-labelled tracer, insoluble in aqueous solvents, is then dissolved in a liquid constituted by a solution of human blood albumin. The use of human blood albumin poses certain problems for reasons of the very strict control to be exercised on the quality of the human blood albumin so as to avoid any viral contamination of the patient. It would therefore be particularly interesting to use, for the solubilisation, a compound that does not present any contamination risks.

Furthermore, the preparation of the fatty acid labelled with iodine-123 is a rather burdensome method, which requires qualified and trained personnel and a sterile environment to ensure that the final product is innocuous.

It would therefore be of interest, in order to improve the quality of the product, to be able to do this in a pharmaceutical establishment which would be able to distribute the radio-labelled product, both sterile and ready for use.

However, when human blood albumin is used to make the product soluble, sterilisation by heat is impossible since the blood albumin is degraded under these conditions.

Specifically, the object of this invention is to replace human blood albumin with a product that does not have the disadvantages described above, with the purpose of obtaining a radio-pharmaceutical composition of a radio-halogenated fatty acid that, in addition, leads to improved biodistribution of the radio-halogenated fatty acid.

This product that replaces the human blood albumin is a cyclodextrin or one of its derivatives.

Cyclodextrins are cyclic oligosaccharides composed of 6(α), 7(β) and 8(γ) units of D-glucopyranose linked α-1,4. In these cyclodextrins, the internal hydrophobic cavity is constituted by protons, while the hydroxyl groups which are directed towards the exterior, generate an external hydrophilic structure. This internal cavity can accept hydrophobic molecules or parts of organic molecules. An inclusion complex is then formed.

This capacity to enclose organic molecules has already been used to solubilise medicines sparingly soluble or insoluble in water, as has been described in U.S. Pat. No. 4,727,064 and EP-A-0 149 197. Hence inclusion complexes have been formed with organic compounds such as hormones, steroids, cardiac glycosides, the derivatives of benzodiazepines, benzimidazoles, piperidines, piperazines, imidazoles etc.

However, as indicated in EP-A-0149197, β-cyclodextrin and its methyl derivatives are not suitable for therapeutic use because of their high toxicity.

Nevertheless, within the field of scintigraphy WO-A-93/15765 describes the use of cyclodextrins as an additive to stabilise certain constituents of a pharmaceutical product kit, notably phosphorated ligands such as tris(3-methoxypropyl) phosphine, against oxidation and volatilisation. In this case, fatty acids are not considered; the radio-element is technetium or rhenium whose chemistry is very different to that of the halogens used in the invention; and the purpose is not to solubilise the radio-pharmaceutical product but to stabilise the constituents such as the phosphorated ligands, in a preparation kit for a radio-pharmaceutical product.

The precise objective of this invention is a radio-pharmaceutical composition including a radio-halogenated fatty acid, in which the fatty acid is in the form of an inclusion complex with a cyclodextrin, which allows the fatty acid to dissolve in an aqueous solution without adding human blood albumin. The composition can be used for the scintigraphic examination of the myocardium.

DETAILED DESCRIPTION OF THE PREFERRED EMBODIMENTS

Figure 1:
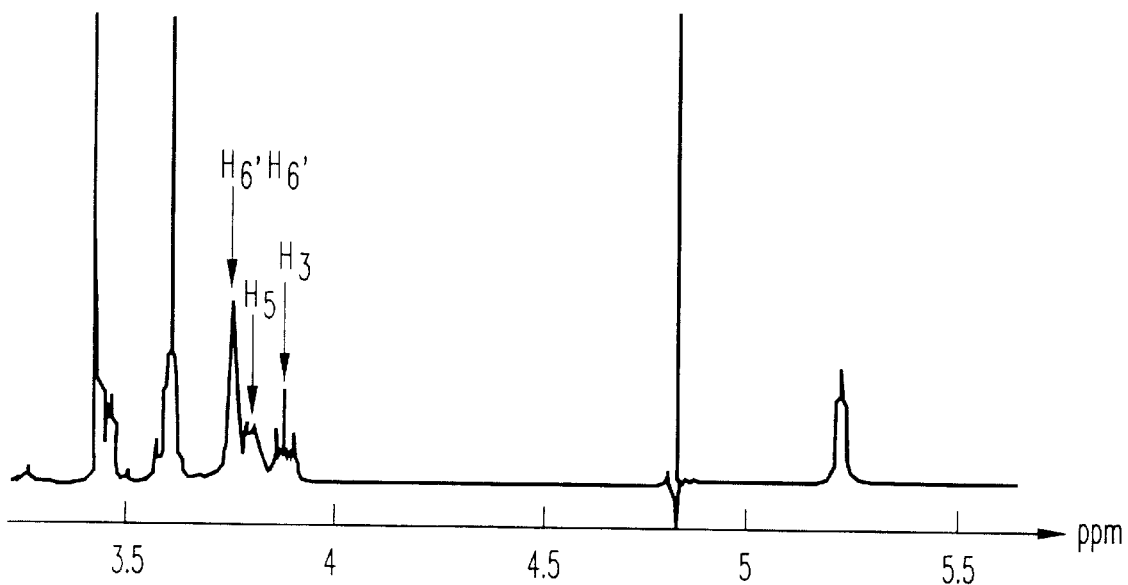
FIG. 1 represents a nuclear magnetic resonance (NMR) spectrum of 2,6-dimethyl β-cyclodextrin at 500 MHz. Specifically, the spectrum is of the inclusion complex dissolved at a concentration of 4 mmol/l in phosphate buffer solution at 298° K.

The cyclodextrins usable in this composition can be of different types and can include various substituents. They are chosen with regard to the properties that this inclusion complex must have, in particular as a radio-pharmaceutical product.

Also, it is chosen a cyclodextrin that is resistant to the sterilisation treatments used and that does not exert any harmful influence on the biodistribution of the fatty acid.

Preferably β and γ-cyclodextrins or their mono- or di-substituted derivatives are used, in particular, alkylated or hydroxyalkylated derivatives. Such derivatives are described, for example, in the book by Dominique Duchêne "New Trends in Cyclodextrins and Derivatives; Publ. de Santé, 1991, pages 269 to 278, and 315 to 319. By way of examples of such derivatives, heptakis-2,6-di-O-methyl-cyclomaltoheptaose, named below as 2,6-dimethyl β-cyclodextrin and heptakis-O-hydroxypropyl cyclomaltoheptaose, named below as hydroxypropyl β-cyclodextrin can be mentioned.

The radio-halogenated fatty acids used in the inclusion complex can equally be of different types. In particular, it can be used saturated or unsaturated aliphatic fatty acids, straight chain or branched chain, that include from 14 to 18 carbon atoms and aromatic fatty acids such as the (iodophenyl) alkanoic acids, used for the examination of the myocardium.

The halogen is generally in the ω position. Furthermore, when the fatty acid is an aliphatic acid, it is advantageously substituted in the β position, in relation to the carboxylic acid group, with one or several alkyl substituents, for example, methyl or ethyl.

Indeed, the metabolisation of the fatty acid through β-oxidation can be slowed by the presence, in the β position of one or two methyl groups. The retention time of the fatty acid in the myocardial cell is thus increased, which allows the scintigraphic examination to be carried out with greater ease.

The radioactive halogen of the fatty acid can be chosen from among the radioactive isotopes of F, Cl, Br and I.

As examples of such isotopes, $^{123}$I, $^{125}$I, $^{131}$I, $^{124}$I, $^{18}$F, $^{76}$Br, $^{82}$Br and $^{34m}$Cl can be mentioned.

As examples of usable fatty acids, 16-iodo 3-methyl hexadecanoic acid, 16-iodo 3,3-dimethyl hexadecanoic acid, 16-iodo 9-hexadecenoic acid, (ortho iodophenyl) pentadecanoic acid, 15-(para-iodophenyl) pentadecanoic acid and 15-(para-iodophenyl) 3-methyl pentadecanoic acid may be mentioned.

The use of fatty acids of this type is described in Eur. J. Nucl. Med., 1988, 14, p. 624–627; Nucl. Med. Biol. Vol. 17, No. 8, 1990, p. 745–749 and Vol. 20, No. 6, 1993, p. 747–754; and Nuclear Medicine Communications, 1993, 14, p. 181–188 and 310–317.

Preferably, the radio-halogenated fatty acid is a 16-halogeno 3-methyl hexadecanoic acid, in particular, 16-iodo 3-methyl hexadecanoic acid (IAGM).

The inclusion complex used in the pharmaceutical compositions of the invention can be prepared by traditional methods, for example, by mixing a solution of radio-halogenated fatty acid in an organic solvent miscible with water, with an aqueous solution of the cyclodextrin used, followed by evaporation of the organic solvent. The aqueous solution can then be evaporated when one wishes to obtain the complex in the dry state.

As an example of a usable organic solvent, acetone can be mentioned.

The quantities of cyclodextrin and radio-halogenated fatty acid present in the mixture must correspond to an excess of cyclodextrin with respect to the fatty acid. For example, quantities of radio-halogenated fatty acid and of cyclodextrin can be used such that the molar ratio cyclodextrin/radio-halogenated fatty acid is from 2 to 10. Generally, good results are achieved with a molar ratio of about 5.

According to a preferred embodiment of the invention, the radio-pharmaceutical composition usable for the examination of the myocardium, is constituted by an aqueous solution of the inclusion complex of the cyclodextrin and the radio-halogenated fatty acid.

The radio-halogenated fatty acid used in the radio-pharmaceutical composition of the invention, can be prepared by a traditional method, for example by the method described in EP-A-0 069 648 when the radioactive halogen is $^{123}$I, $^{125}$I, $^{131}$I or $^{124}$I.

In order to obtain the radio-pharmaceutical composition, the radio-halogenated fatty acid, previously brought to dryness, is taken up again in an aqueous solution of cyclodextrin.

After dividing up into volumes of 2 ml, each flask can be subjected to sterilisation; this can be carried out by traditional methods, for example, by heating.

In the radio-pharmaceutical composition, the aqueous solution contains preferably, other additives, in particular in order to bring the osmolarity to a value suitable for the injection.

The additives used for this purpose can be buffers, physiological salt solution and, in particular, polyols. As examples of usable polyols, mannitol, inositol, sorbitol and dixylitol can be mentioned.

The additives are chosen in relation to the possible processes to which the solution will be subjected, in particular the method of sterilisation that is comtemplated.

When the sterilisation is carried out through heat, preferably a polyol such as mannitol or inositol is used.

A further subject of the invention is a kit for the preparation of a radio-pharmaceutical composition with radioactive iodine, from a non-radioactive fatty acid and cyclodextrin.

This kit includes at least two flasks which contain respectively just one or several of the following constituents:

a non-radioactive iodated or brominated fatty acid, an organic solvent such as acetone, a metallic iodide such as sodium iodide, a cyclodextrin, and an excipient suitable for the preparation of an injectable solution.

With this kit, first of all, the fatty acid labelled with radioactive iodine by using the method described in EP-A-0 069 648 can be prepared from the flask or flasks containing the non-radioactive fatty acid, the metallic iodide and the organic solvent, the contents of which are combined with the radioactive iodine.

After this operation, the fatty acid labelled with radioactive iodine is mixed with an aqueous solution of cyclodextrin from one of the flasks in the kit.

Other characteristics and advantages of the invention will become more apparent on reading the following examples.

EXAMPLES 1 to 4

Solubilisation of 16-Iodo-3-Methyl Hexadecanoic Acid in Different Cyclodextrins.

In these examples, 1 mg (2.5 μmol) of 16-iodo-3-methyl hexadecanoic acid (IAGM) was dissolved in 500 μl of acetone. After partial evaporation of the acetone, one equivalent of the cyclodextrin used (2.5 μmol) dissolved in 500 μl of 0.1M phosphate buffer solution, at pH 7.4, was added. It is stirred vigorously while heating. After cooling, development of the solution is watched. When it remains unchanged with time, the solubility limit has been reached. In the contrary case, 1, then 2, then 3 equivalents etc. are added in order to obtain the desired solution.

The results obtained with different cyclodextrins are summarised in Table 1 below.

In this table, the equivalents of cyclodextrin required to obtain a clear solution have been shown.

The results in Table 1 show that 2,6-dimethyl β-cyclodextrin and 2-hydroxypropyl β-cyclodextrin gave the best results. Good results were also obtained with the γ-cyclodextrin. On the other hand, no complex was obtained with 2,3,6-trimethyl β-cyclodextrin.

The complex obtained with 2,6-dimethyl β-cyclodextrin was studied through nuclear magnetic resonance (NMR) of the proton at 500 MHz. The spectrum obtained with the inclusion complex dissolved at a concentration of 4 mmol/l in the phosphate buffer solution at 298K is represented in FIG. 1.

Figure 2:
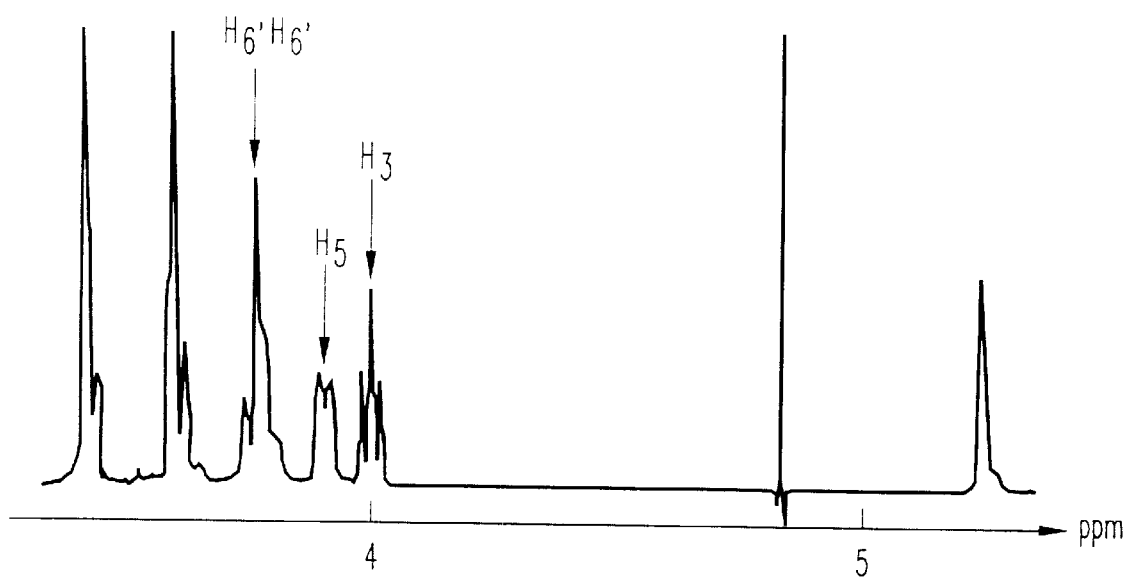
FIG. 2 represents the NMR spectrum of the complex as in FIG.1, except at a concentration of 10 mmol/l in the same phosphate buffer.

In FIG. 2, for purposes of comparison, the NMR spectrum of the proton at 500 MHz of the 2,6-dimethyl β-cyclodextrin alone has been represented at a concentration of 10 mmol/l in the same phosphate buffer.

The comparison of these two spectra shows that an inclusion complex has indeed been produced, since a displacement of the $H^3$ and $H^5$ protons towards the strong fields is observed; hence the protons situated in the internal cavity are disturbed by the included compound. The inclusion of the fatty acid occurs via the halogen followed by some $CH_2$ groups.

A study in a dimethylsulphoxide medium (DMSOd6) has provided evidence of a 1/1 stoichiometry for the complex and an association constant of 500.

EXAMPLES 5 to 14

Stability of Different Complexes to Sterilisation by Heating.

In these examples, different cyclodextrin complexes were prepared with 16-iodo 3-methyl hexadecanoic acid (IAGM) in the following way. 10.1 μmol of the cyclodextrin mentioned in Table 2 below, dissolved in 2 ml of the solvent also mentioned in Table 2, was added to a flask containing 2.02 μmol of IAGM. The solution was subjected to sterilisation by heat under the conditions given in Table 2.

The radio-chemical purity of the complex was determined before sterilisation and after sterilisation. This radio-chemical purity (as a %) corresponds to the percentage of radioactivity present in the complex in relation to the total radioactivity.

The results are given in Table 2.

In view of these results, it is noted that the dissolution solvent for the cyclodextrin is of great importance. In effect, in the presence of chloride ions or carbonate ions, the radio-chemical purity is very much lower after sterilisation, which is not the case with water. The best solvents are water and the solutions of mannitol and inositol at 4% in water. The osmotic pressures of the two latter solvents being between 280 and 300 mOsm/kg, these solutions can be used for the manufacture of injectable radio-pharmaceutical products.

EXAMPLE 15

Study of the Cardiac Fixation of the Inclusion Complex of 16-Iodo 3-Methyl Hexadecanoic Acid (IAGM) with 2,6-Dimethyl-β-Cyclodextrin.

In this example, Beagle dogs weighing 15 to 18 kg, were injected with 2 ml of an aqueous solution of the inclusion complex obtained by dissolving 0.8 mg of 16-iodo 3-methyl hexadecanoic acid, labelled with iodine-123 (74 MBq.) in a solution of inositol at 4% in water (ppi) containing 14 mg of 2,6-dimethyl-β-cyclodextrin.

The aqueous solution was prepared using the procedure described for Example 5 and then sterilised by heating to 120° C. for 20 min.

The fatty acid labelled with iodine-123 was prepared in the following way.

8 mg of fatty acid was dissolved in an acetone solution containing 10 μg of iodine-127. The solution was added to the iodine-123 solution (1850 MBq. at calibration). The mixture was held at 100° C. for 7 minutes. After cooling, the solution was purified on anionic resin AG 1×8 100–200 mesh. The recovered acetone solution was reduced to dryness. The solid residue was taken up again in 20 ml of a 4% mannitol or inositol solution containing 144 mg of 2,6-dimethyl-β-cyclodextrin. After total dissolution, the solution was divided up into flasks (2 ml per flask). Each flask was crimped and subjected to sterilisation by heating.

After the injection, the dogs were examined using a camera taking one image per minute in order to determine the captation and the retention of the fatty acid labelled with the iodine-123.

The results obtained are given in Table 3 appended.

They were evaluated from digitised values, determined from the images, by using the calculation method described in Eur. J. Nucl. Med., 1988, 14: p. 624–627.

In this table, the captation index is the ratio between the radioactivity present in the heart at 2 min. (in cpm/pixel) over the activity in circulation (in cpm/pixel).

The retention percentages at 30 minutes and at 60 minutes correspond to the ratio between the cardiac radioactivity (after subtraction of the activity in circulation) at 30 minutes or at 60 minutes and the cardiac radioactivity at 10 minutes.

EXAMPLE 16

The same procedure was followed as for Example 15 in order to study the cardiac fixation of the same inclusion complex while replacing the aqueous solution of inositol by a solution of mannitol at 4% in water ppi.

The results obtained are also given in Table 3.

In this table, the results obtained when the dogs were injected with 5 ml of a solution of 16-iodo 3-methyl hexadecanoic acid (8 mg) labelled with iodine-123 (74 MBq.) dissolved in a carbonate/hydrogen carbonate buffer, pH=9, with human blood albumin.

The results in Table 3 show that a good cardiac fixation was obtained.

Furthermore, it was noted on the images that the hepatic fixation, 15 to 20 minutes after the injection, was lower with the solutions of the invention than that obtained with the solution of human blood albumin.

Hence the use of the cyclodextrin allows, not only to avoid the risks of viral contamination, but also to improve the biodistribution of the fatty acid.

TABLE 1

| Ex. | Cyclodextrin | Equivalents of cyclodextrin/mass of fatty acid | Observations |
|---|---|---|---|
| 1 | 2,6-dimethyl β cyclodextrin | 5 eq./16.6 mg | colourless clear solution |
| 2 | 2,3,6-trimethyl β cyclodextrin | — | solution permanently opalescent |

TABLE 1-continued

| Ex. | Cyclodextrin | Equivalents of cyclodextrin/mass of fatty acid | Observations |
|---|---|---|---|
| 3 | 2-hydroxypropyl β cyclodextrin | 5 eq./21.3 mg | colourless clear solution |
| 4 | γ-cyclodextrin | 7 eq./24.9 mg | clear solution |

TABLE 2

| | | | Radio chemical purity (%) | |
|---|---|---|---|---|
| Ex. | Cyclodextrin | Sterilisation | Solvent for the cyclodextrin | before sterilisation | after sterilisation |
| 5 | 2-hydroxypropyl β-cyclodextrin | 110° C. 30 min | Aqueous $CO_3^-/HCO_3^-$ buffer pH = 9 | 92.5 | 75.8 |
| 6 | 2-hydroxypropyl β-cyclodextrin | 110° C. 30 min | Aqueous phosphate buffer pH = 7.4 | 97.2 | 91.3 |
| 7 | 2-hydroxypropyl β-cyclodextrin | 110° C. 30 min | Aqueous 0.5 ml phosphate buffer + 0.5 ml phosphate buffer in physiological salt solution pH = 7.4 | 91.4 | 69.2 |
| 8 | 2,6-dimethyl β-cyclodextrin | 110° C. 30 min | $H_2O$ | 92.6 | 86.7 |
| 9 | 2,6-dimeethyl β-cyclodextrin | 120° C. 20 min | $H_2O$ | 99.1 | 98 |
| 10 | 2,6-dimethyl β-cyclodextrin | 120° C. 20 min | 1 ml $H_2O$ + 1 ml physiological salt solution | 99.4 | 91.7 |
| 11 | 2,6-dimethyl β-cyclodextrin | 120° C. 20 min | $H_2O$ | 99.3 | 97.2 |
| 12 | 2,6-dimethyl β-cyclodextrin | 120° C. 20 min | 4% mannitol solution | 92.8 | 88.7 |
| 13 | 2,6-dimethyl β-cyclodextrin | 120° C. 20 min | 4% mannitol solution | 99.8 | 96.1 |
| 14 | 2-hydroxypropyl β-cyclodextrin | 110° C. 30 min | $H_2O$ | 97.6 | 91.2 |

TABLE 3

| EXAMPLES | COMPARATIVE EXAMPLES | 15 | 16 |
|---|---|---|---|
| Product injected | IAGM with HBA | IAGM with inositol | IAGM with mannitol |
| Captation index | 0.54 | 0.55 | 0.75 |
| Retention at 30 min (%) | 70 | 71 | 74 |
| Retention at 60 min (%) | 69 | 55 | 64 |

We claim:

1. The radio-pharmaceutical composition, comprising: a radio-halogenated fatty acid in the form of an inclusion complex with a cyclodextrin.

2. The composition according to claim 1, wherein said cyclodextrin is a β-cyclodextrin, a γ-cyclodextrin or a derivative thereof.

3. The composition according to claim 2, wherein said cyclodextrin is hepatis-2,6-di-O-methyl-cyclomaltoheptaose.

4. The composition according to claim 2, wherein said cyclodextrin is hepatis-O-hydroxypropyl cyclomaltoheptaose.

5. The composition according to claim 1, wherein said fatty acid is a $C_{14-18}$ ω-radio-halogenated aliphatic fatty acid, optionally mono- di-substituted in the β position by one or two alkyl groups, or an aromatic fatty acid.

6. The composition according to claim 1, wherein the radioactive halogen atom of the fatty acid is selected from the group consisting of the radioactive isotopes of F, Cl, Br and I.

7. The composition according to claim 6, wherein said halogen is $^{123}I$, $^{125}I$, $^{131}I$ or $^{124}I$.

8. The composition according to claim 1, wherein said fatty acid is 16-iodo 3-methyl hexadecanoic acid.

9. The composition according to claim 1, comprising an aqueous solution of the inclusion complex of said cyclodextrin and said radio-halogenated fatty acid.

10. The composition according to claim 9, further comprising at least one other additive to bring the osmolarity of the aqueous solution to a value suitable for injection.

11. The composition according to claim 10, wherein said additive is inositol or mannitol.

12. The method of preparing of a radio-pharmaceutical composition according to claim 1, comprising mixing a radio-halogenated fatty acid reduced to dryness with an aqueous solution of cyclodextrin.

13. The method according to claim 12, wherein solution obtained is subjected to sterilization by heating.

14. The method according to claim 12, wherein quantities of said radio-halogenated fatty acid and said cyclodextrin are used such that the molar ratio of the cyclodextrin to the radio-halogenated fatty acid is from 2 to 10.

15. The method according to claim 12, wherein the aqueous solution of cyclodextrin further comprises a buffer or a polyol or a mixture thereof in order to adjust osmolarity of the solution.

16. The method according to claim 13, wherein said additive is a polyol.

17. The method according to claim 16, wherein said additive is inositol or mannitol.

18. The kit for the preparation of a radio-pharmaceutical composition, comprising at least two flasks and the following constituents:
  a non-radioactive iodated or brominated fatty acid;
  an organic solvent;
  a metallic iodide;
  a cyclodextrin; and
  an excipient suitable for the preparation of an injectable solution.

19. The kit according to claim 18, wherein said fatty acid is 16-iodo 3-methyl hexadecanoic acid.

20. The kit according to claim 19, wherein said cyclodextrin is heptakis-2,6-di-O-methyl-cyclo-maltoheptaose or hepatis-O-hydroxypropyl cyclomaltoheptaose.

* * * * *